United States Patent
Costa et al.

(10) Patent No.: US 8,072,605 B2
(45) Date of Patent: Dec. 6, 2011

(54) METHOD AND APPARATUS FOR DETERMINING QUALITY OF FRUIT AND VEGETABLE PRODUCTS

(75) Inventors: Guglielmo Costa, Bologna (IT); Massimo Noferini, Borgo Tossignano (IT); Giovanni Fiori, Ascoli Piceno (IT)

(73) Assignee: Alma Mater Studiorum — Universita di Bologna, Bologna (IT)

( * ) Notice: Subject to any disclaimer, the term of this patent is extended or adjusted under 35 U.S.C. 154(b) by 631 days.

(21) Appl. No.: 11/990,274

(22) PCT Filed: Aug. 4, 2006

(86) PCT No.: PCT/IB2006/002143
§ 371 (c)(1),
(2), (4) Date: May 13, 2008

(87) PCT Pub. No.: WO2007/017732
PCT Pub. Date: Feb. 15, 2007

(65) Prior Publication Data
US 2009/0147260 A1 Jun. 11, 2009

(30) Foreign Application Priority Data
Aug. 10, 2005 (IT) .............................. MO2005A0211

(51) Int. Cl.
*G01N 21/55* (2006.01)
(52) U.S. Cl. ...................................................... 356/445
(58) Field of Classification Search .................. 356/432, 356/433, 445, 448
See application file for complete search history.

(56) References Cited

U.S. PATENT DOCUMENTS

| | | | | |
|---|---|---|---|---|
| 2,933,613 A | * | 4/1960 | Powers | 250/214 R |
| 4,037,048 A | * | 7/1977 | Walker | 348/164 |
| 4,095,696 A | * | 6/1978 | Sherwood | 209/558 |
| 4,476,982 A | * | 10/1984 | Paddock et al. | 209/582 |
| 5,471,311 A | * | 11/1995 | van den Bergh et al. | 356/446 |
| 5,675,419 A | * | 10/1997 | Van Den Bergh et al. | 356/446 |
| 5,822,068 A | * | 10/1998 | Beaudry et al. | 356/417 |
| 6,080,950 A | * | 6/2000 | Jalink | 209/577 |
| 6,512,577 B1 | * | 1/2003 | Ozanich | 356/73 |
| 6,563,122 B1 | * | 5/2003 | Ludeker et al. | 250/458.1 |
| 6,847,447 B2 | * | 1/2005 | Ozanich | 356/326 |
| 7,316,322 B2 | * | 1/2008 | Kawabata et al. | 209/509 |
| 2002/0011567 A1 | * | 1/2002 | Ozanich | 250/326 |

FOREIGN PATENT DOCUMENTS
WO 00/79243 12/2000
WO 02/088678 11/2002

OTHER PUBLICATIONS

International Search Report for PCT/IB2006/002143 mailed Mar. 8, 2007.

(Continued)

*Primary Examiner* — Roy M Punnoose
(74) *Attorney, Agent, or Firm* — Nixon & Vanderhye P.C.

(57) ABSTRACT

A method for determining the quality and ripeness of fruit and vegetable products includes the steps of irradiating a fruit or vegetable product with radiating light; measuring the absorbance of the product at the wavelengths of 670 nm and 720 nm; determining the difference of absorbances measured at the wavelengths of 670 nm and 720 nm.

30 Claims, 7 Drawing Sheets

OTHER PUBLICATIONS

Zude-Sasse, M. et al., "An Approach to Non-Destructive Apple Fruit Chlorophyll Determination", Postharvest Biology and Technology 25, vol. 25, No. 2, pp. 123-133, (2002).

Hernandez-Martinez, R., et al., "Detecting Internal Breakdown in Nectarines and Peaches Using Optical Measurements", Acta Horticulturae, vol. 599, pp. 351-357, (2003).

Mehinagic, E. et al., "Prediction of the Sensory Quality of Apples by Physical Measurements", Postharvest Biology and Technology, vol. 34, No. 3, pp. 257-269, (Dec. 2004).

Flores, F., et al., "The Use of Ethylene-Suppressed Lines to Assess Differential Sensitivity to Ethylene of the Various Ripening Pathways in Cantaloupe Melons", Physiologia Plantarum, vol. 113, No. 1, pp. 128-133, (Sep. 2001).

Zerbini et al., "Time-Resolved Reflectance Spectroscopy as a Non-Destructive Tool to Assess the Maturity at Harvest and to Model the Softening of Nectarines", Proc. $5^{th}$ Int. Postharvest Symp., Eds. F. Mencarelli and P. Tonutti, ISHS 2005, pp. 1459-1464.

\* cited by examiner

METHOD AND APPARATUS FOR DETERMINING QUALITY OF FRUIT AND VEGETABLE PRODUCTS

CROSS-REFERENCE TO RELATED APPLICATIONS

This application is the U.S. national phase of International Application No. PCT/IB2006/002143, filed 4 Aug. 2006, which designated the U.S. and claims priority to Italy Patent Application No. MO2005A000211, filed 10 Aug. 2005, the entire contents of each of which are hereby incorporated by reference.

BACKGROUND AND SUMMARY

Description

The invention relates to a method and an apparatus for determining the quality of fruit and vegetable products. The prior art comprises various methods and apparatuses for determining the quality of fruit and vegetable products.

In international patent application WO-00/02036 there is illustrated a method for determining the ripeness and the quality of fruit and berries by measuring the quantity of fluorescence of the chlorophyll and an apparatus for classifying fruit and berries. The method is based on the determination of the quantity of fluorescence of the chlorophyll of the fruit and of the berries. The method provides for inducing fluorescence in the molecule of the chlorophyll by irradiating the fruit and the berries with electromagnetic radiation at a suitable wave length and measuring the degree of fluorescence.

As the intensity of the fluorescence of chlorophyll is directly connected to the quantity of chlorophyll, it is possible to grade the fruit and the berries by ripeness and quality on the basis of the quantity of chlorophyll contained in the fruit.

In this document, measuring chlorophyll is used to assess the ripeness of small fruit such as bilberry, when it is in a frozen state. It is thus a specific and very limited application, furthermore, the apparatus for applying the method is rather complex and it is not portable.

In U.S. Pat. No. 5,822,068 there is disclosed a non-destructive test method for testing fruit and vegetables for assessing the quality thereof after harvest (compactness, structure, aroma and colour) using the intensity of the fluorescence of the skin or of the leaves. A source of low-intensity red light is used to irradiate the skin or the leaves of certain plants belonging to varieties of fruit or vegetables to provide a first level of fluorescence intensity above that of red light in the range between 710 nm and 740 nm.

A second source of high-intensity red light is used to produce a second maximum intensity of fluorescence in the skin or in the leaves, still in the range between 710 nm and 740 nm.

By means of the ratio between the "difference of the first level of fluorescence intensity" and "the second intensity" a measurement of the quality of the fruit or of the vegetables is obtained.

In U.S. Pat. Nos. 6,512,577 and 6,847,447 there are disclosed an apparatus, method and techniques for measuring and correlating the features of the samples of fruit with the visible and/or near infrared radiation spectrum. The methods and the apparatuses of these two patents use, in samples containing molecules of N—H, C—H and O—H, including the fruit, rays with wavelengths in the 250 nm to 1150 nm range to assess one or more parameters, for example contained in soluble solids, hardness of the pulp, acidity, density, pH, colour and to measure external and internal defects, diseases, comprising, for example, dents at the skin level or also below, scars, sunburn, holes.

Known methods and apparatuses for determining the quality of fruit and vegetable products have certain drawbacks.

Known methods and apparatuses are rather complex to make and use, often they are not portable. Long series of preparation or calibration tests are necessary, i.e. hundreds of destructive tests, on each type of fruit or vegetable product to be able to obtain a prevention model to use for subsequent checks of the products the quality of which has to be assessed. Furthermore, each time that the batch of fruit or vegetables is changed, it is necessary to repeat calibration.

Known methods and apparatuses for determining the quality of fruit and vegetable products are often usable only for some specific types of fruit and vegetables and are unable to provide reliable results, so the checks on the fruit and vegetable products do not allow an effective assessment of the quality of the products.

Further, known methods and apparatuses for determining the quality of fruit and vegetable products give values that are affected by the temperature of the products, so that it is necessary to compensate the temperature for the measurements taken, but this compensation does not always provide reliable values.

An object of the invention is to improve the known methods and apparatuses for determining the quality of fruit and vegetable products.

Another object is to make a method and an apparatus available for determining the quality of fruit and vegetable products that provide reliable and credible assessments of the quality of the fruit and vegetable products.

A further object is to make an apparatus available for determining the quality of fruit and vegetable products that is actually portable.

Still another object is to make a method and an apparatus available for determining the quality of fruit and vegetable products that are independent of the temperature of the products.

Still another object is to simplify the methods and the construction of the prior-art apparatuses for determining the quality of fruit and vegetable products.

In a first aspect of the invention, there is provided a method for determining the quality of fruit and vegetable products, comprising the following steps: —irradiation of a fruit or vegetable product with radiating light; —measurement of the penetrating radiation and the radiation reflected back by the product, characterised in that said measuring is performed at the wavelengths of 670 nm and 720 nm.

In a second aspect of the invention, an apparatus is provided for determining the quality of fruit and vegetable products comprising a radiating light source, a sensor for receiving part of the radiation reflected by the fruit and vegetable products connected to a detecting device, a central control and processing unit for processing the signals received from the detecting device and a display for displaying the results of the reprocessed signals, wherein the detecting device detects the radiation reflected by the fruit and vegetable products at the wavelengths 670 nm and 720 nm.

Owing to the first and second aspect of the invention it is possible to obtain a substantial simplification of the apparatus and method for determining the quality of the fruit and vegetable products. Owing to the simplification, greater reliability and greater precision of the results of examinations of the fruit and vegetable products are obtained, costs are also contained.

BRIEF DESCRIPTION OF THE DRAWINGS

The invention can be better understood and implemented with reference to the enclosed drawings, which show some exemplifying and non-limitative embodiments, in which.

DETAILED DESCRIPTION OF TECHNOLOGY

Figure 1:
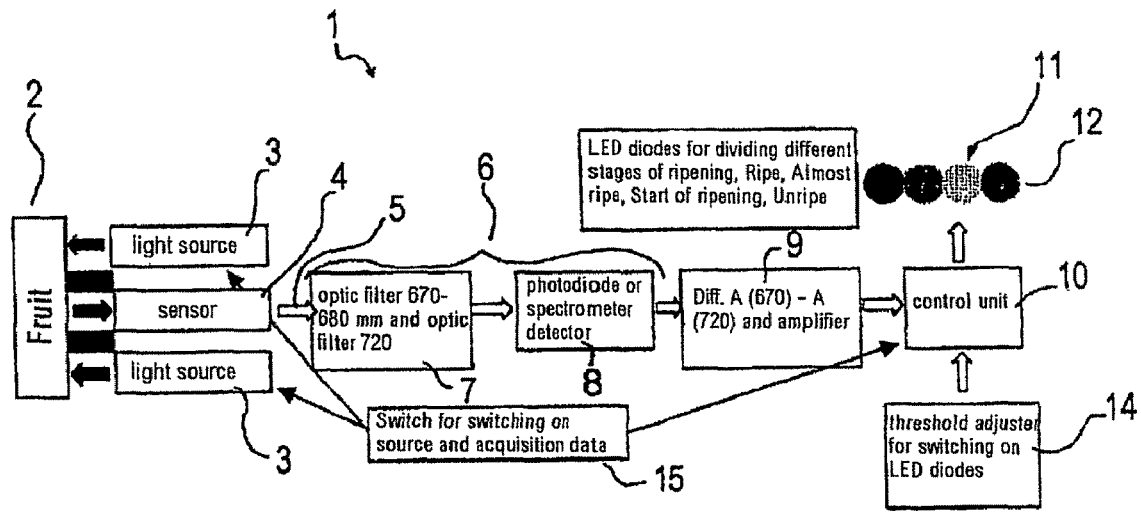
FIG. 1 is a schematic block diagram that illustrates a first embodiment of the apparatus for determining the quality of fruit and vegetable products according to the invention.

With reference to FIGS. 1-4, with 1 there is indicated an apparatus for determining the quality of fruit and vegetable products 2, such as fruit and vegetables. In the description that follows explicit reference will be made to determining the quality of a fruit 2, even if the invention can also be applied to other similar products such as vegetables, etc.

Certain known concepts relating to light, or luminous radiation, and to absorbance are now introduced that are necessary for defining the invention better.

Light consists of photons that move with a rectilinear undulating motion. If the photons meet an obstacle, changes in the direction of the motion of the light are observed. The different direction is caused by the effects of: reflection, refraction, interference, diffraction.

Light is able to spread in space at a constant speed C (300000 km per second) with a repeated pattern defined by the wavelength ($\lambda$) expressed in submultiples of a meter. A determined number of waves will pass through a point of space: this number is said frequency ($\nu$) expressed in units of time ($\sec^{-1}$ or Hz).

A proportionality relationship exists between wavelength and frequency: $C=\lambda*\nu$.

The wavelength can thus be calculated by knowing the frequency, there exists in fact an inverse proportionality between the wavelength and the frequency. Between current intensity and light intensity there exists a relationship that can be exploited for measurements. This relationship is achieved by means of a phototube that that transforms a light signal into an electric signal. The phototube is based on the photoelectric principle according to which when a light beam hits particular materials there is an excitation to which the surface of the material responds in "electric" terms with excitation of electrons the number of which corresponds to the intensity of the penetrating radiation.

Whatever the light source, we will never have a luminous radiation but several radiations, each with a wavelength proper to it. Although the term "light" was originally linked to the electromagnetic radiation that is visible to the human eye, it has become commonly used in an extended sense to indicate all electromagnetic radiation. Subsequently in this description, all electromagnetic radiation is indicated by the term "light" or "luminous radiation".

To divide white light—as group of all the visible colours—a prism is used that refracts the penetrating light and decomposes it. In order to obtain better dispersion of the penetrating light, the prism can be machined to create grooves in a small plate of transparent material, obtaining heightened diffraction. This is the so-called reticule system.

In each molecule of a substance there is absorption of luminous radiation, said absorption is due to a shift of electrons of the molecule from a level to the superior level; this absorption occurs for all the molecules of the same substance.

It can also be affirmed that a certain substance absorbs radiation of a single given wavelength. For this reason, each single substance has a specific luminous radiation of specific wavelength. The greater the energy necessary for a given passage from a level to another level of electrons, the higher will be the frequency of the corresponding light.

Obtaining absorption spectra is thus an excellent method for identifying substances and for interpreting the molecular structure from the geometric and chemical point of view.

If the absorption of light energy of a substance in function of the wavelength of a transmitted radiation is shown on a graph, maximum absorption will be at the wavelength that is characteristic of the substance, i.e. maximum absorption will be obtained when radiant energy causes the electrons to move from a level to another. Absorption decreases the further it moves away from the characteristic wavelength with a bell curve trend (Gauss curve). This curve, which is characteristic for each substance, is called "absorption curve or spectrum" and represents the optic properties of the substance.

The foregoing remarks also apply to the substance in solution and this enables the concentration of solution to be identified by making a ratio between the penetrating light (Io) and the emerging light (I).

This ratio is called transmittance: (T)=Io/I

The decimal logarithm of the transmittance:

$$A=\log(I/Io)$$

is defined as absorbance (A) or optical density (O.D.) or extinction (E). This principle, which is known as the Beer-Lambert law, enables the concentration of a solution to be identified that is able to absorb a certain wavelength zone.

To obtain the absorption spectra, a reference spectrum has to be recorded first, i.e. a spectrum obtained by irradiating a completely white object (Io), and placing it in relation to a spectrum (I) of a fruit, obtained in a similar manner, replacing the completely white object with the fruit.

The invention is based on the determination of absorption at only two wavelengths that occur in a fruit. In particular, the invention is based on the measurement of absorbance at 670 nm and at 720 nm in a fruit, these values correspond to the maximum and minimum absorption value of chlorophyll, as is better explained below.

The apparatus 1 essentially comprises a light source 3 with at least a wavelength centred on 670 nm with a range of more or less 50 nm. The light source 3 can be realised with LED diodes, or with a laser, or can be realised with a white light source, for example a halogen lamp.

In the latter case, the light source 3 emits radiation that comprises the entire wavelength of white light.

The version of the apparatus 1 realised with LED diodes comprises at least two LED diodes that emit radiation only within the wavelengths 670 nm and 720 nm. With the LED diodes the request for energy is very limited, and this type of light source is therefore particularly indicated for the apparatus 1 in the portable version.

The apparatus 1 furthermore comprises a sensor 4, which is arranged for being placed in contact with the fruit 2, the sensor 4 is connected to a detecting device 6 through an optic fibre beam 5 suitable for conveying a return light signal from the fruit 2. The sensor 4 furthermore has a separating element 4a that prevents radiation originating from the source 3 from reaching the sensor 4 directly without passing through the fruit 2.

The visual field of the sensor 4 is separated by the lighted surface from the light source 3, by means of a sealed contact in contact with the surface of the fruit 2, this manner of detecting the return radiation from the fruit is also called "interactance".

The separating element 4a may comprise a ring in soft rubber, or a flexible cuff, arranged for being placed in contact with the fruit 2 without damaging it.

By isolating the sensor 4 from the radiation coming from the light source 3, from the ambient light and also from the light reflected by the surface of the fruit, the problem of grading a fruit on the basis of the colour is avoided. In fact, the surface colour of the fruit is often not necessarily linked to the state of ripeness.

The detecting device 6 comprises an optic filter 7 and a detector 8. The detector 8 can be realised with a photodiode or with a spectrometer. The return radiation from the fruit 2 comprises radiation on various wavelengths, the optic filter 7 filters only two wavelengths at 670 nm and 720 nm.

If the detector 8 is a spectrometer, it is not necessary to provide an optic filter 7, because the spectrometer can select only the two wavelengths at 670 nm and 720 nm.

Even if the detector 8 is represented by a photodiode the energy requirement is limited and thus the photodiode is particularly suitable for the apparatus in a portable version.

The absorption signals at the wavelengths at 670 nm and 720 nm that are thus detected are then differentiated by a differentiating and amplifying device 9, thereby obtaining a low-intensity signal that corresponds to the absorbance difference at the two aforesaid wavelengths. The aforesaid difference is defined as AD (Absorbance difference) as is explained better subsequently. The signal AD is subsequently amplified by the differentiating and amplifying device 9 and sent to a central control and processing unit 10.

The central control and processing unit 10 processes the signal of the absorbance difference AD and by means of a suitable algorithm correlates it with the quality features of the fruit, ethylene concentration, hardness of the pulp, Brix grades, etc.

On the basis of the value of the aforesaid features and the variety of the fruit, the fruit is classified: for example ripe, unripe, to be conserved, etc., and a corresponding signal is generated.

The aforesaid signal processed by the central unit 10 is sent to a display 11 that may comprise a plurality of LED diodes 12, or a screen 13, that provide information on the quality of the examined fruit. In the version illustrated in FIG. 1 there is furthermore provided an adjusting unit 14 that enables the thresholds to be adjusted at which the LED diodes 12 light up.

The apparatus 1 furthermore comprises a switch 15 that simultaneously switches on the light source 3 and the data acquisition part, i.e. the detector 8, the differentiating and amplifying device 9, the central unit 10 and the display 11. In this way the energy requirement for running the apparatus 1 is limited.

Figure 2:
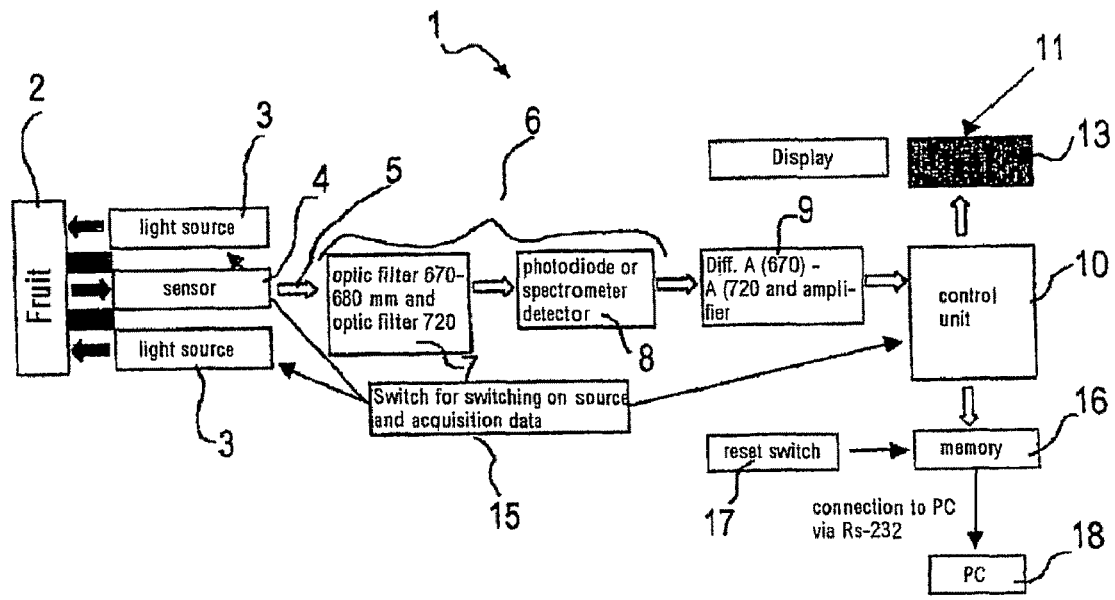
FIG. 2 is a schematic block diagram that illustrates a second embodiment of the apparatus for determining the quality of fruit and vegetable products according to the invention.

In the version illustrated in FIG. 2, the apparatus 1 comprises a memory device 16 that stores the measurements taken with a reset switch 17.

The memory device 16, through suitable interface, for example a Rs-232 connection, can be connected to a computer 18.

Suitable electric supply circuits for the light source 3 and the other parts of the apparatus complete the apparatus 1. In particular, the light source 3 supply comprises a supply stabilising device that maintain a constant level of light radiation emissions. These electric supply circuits are of known type and are not therefore disclosed in detail.

Figure 3:
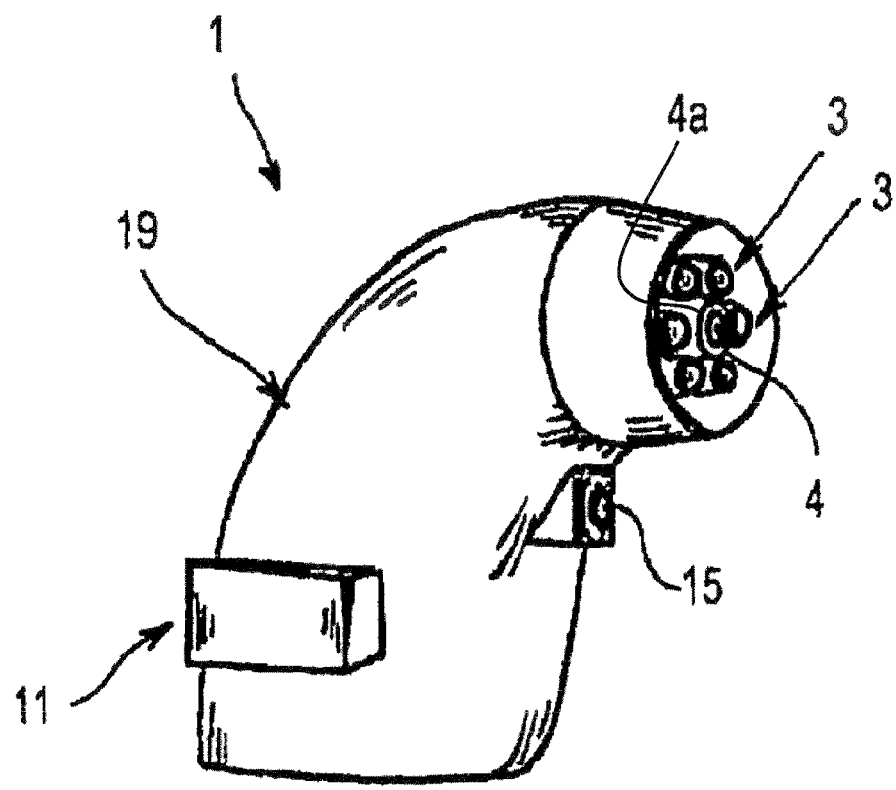
FIGS. 3 and 4 illustrate respectively a lateral perspective view and a frontal view of an apparatus for determining the quality of fruit and vegetable products according to the invention.
Figure 4:
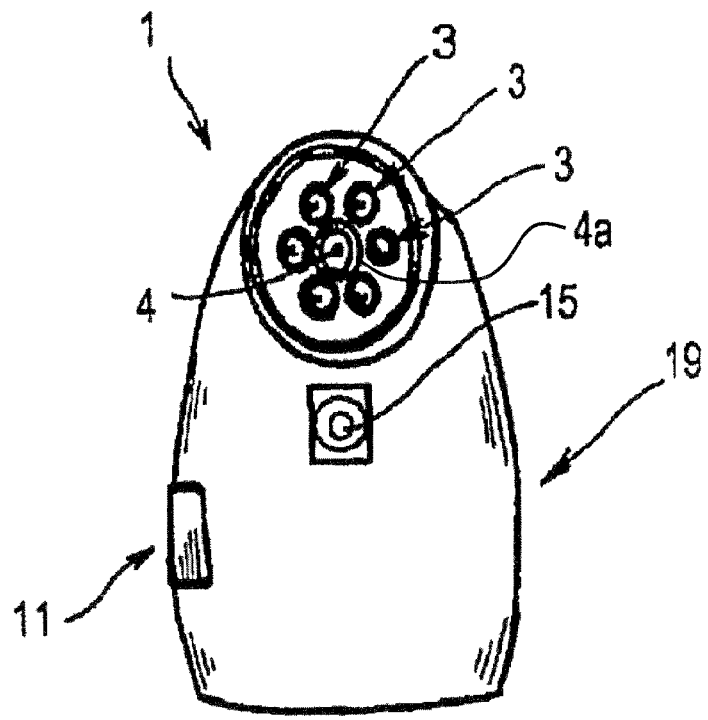

FIGS. 3 and 4 illustrate the apparatus 1 in a portable version. The apparatus comprises a casing 19 that completely encloses all the components of the apparatus 1 and also comprises a battery-powered electricity supply (not shown) that make the apparatus 1 usable for measurements in the field of fruit that is still attached to the tree.

In this version, the display 11 comprises a plurality of LED diodes 12, each of a different colour. For example, each LED diode 12 identifies a different stage of ripeness of the fruit: unripe, green LED diode, starting to ripen, yellow LED diode, almost ripe, orange LED diode, ripe, red LED diode.

The method according to the invention comprises the steps of: —irradiation of a fruit or vegetable product 2 with light radiation with at least a wavelength centred on a wavelength value of 670 nm with a range of more or less 50 nm; —measurement of the radiation reflected by the product 2 at two wavelengths 670 nm and 720 nm; —calculation of the difference in the absorbance value between the values of the wavelengths at 670 nm and at 720 nm, obtaining from said difference an index AD the value of which is correlated with the different parameters that provide a measurement of product quality: soluble solids content, hardness of the pulp, ethylene concentration, etc.

As mentioned above, the invention is based on determination of the absorbance at 670 nm and at 720 nm.

Figure 5:
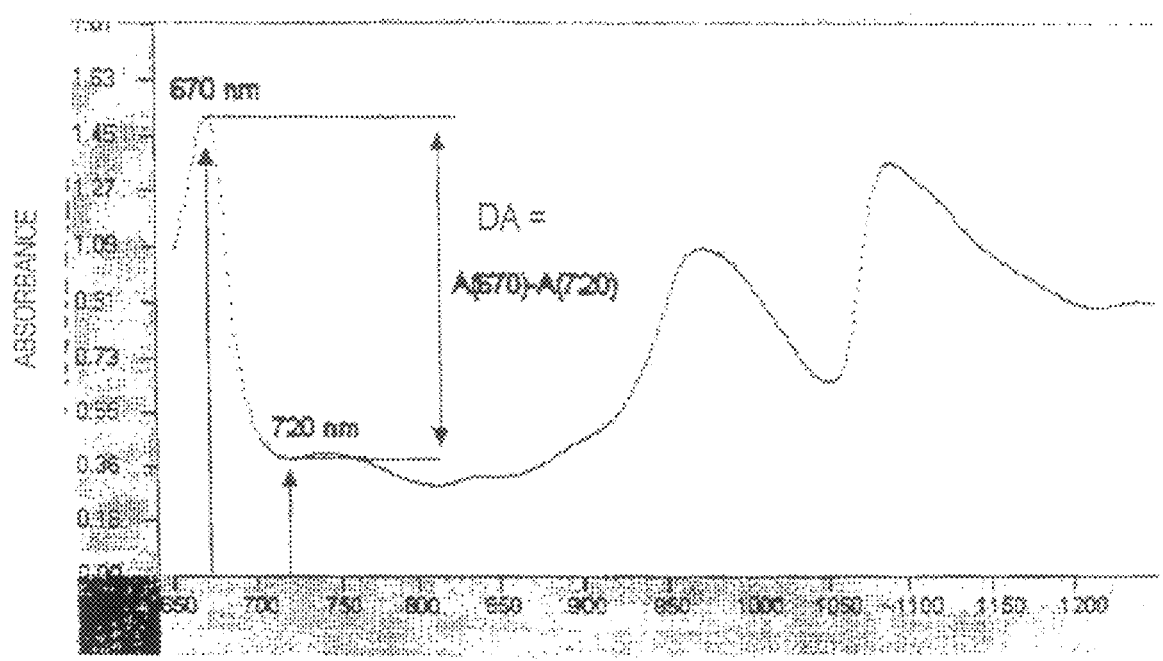
FIG. 5 illustrates a diagram of the absorbance of chlorophyll in function of the wavelength of electromagnetic radiation.

In FIG. 5, which illustrates the absorption spectrum of chlorophyll for a generic fruit, it can be seen that at 670 nm there is the point of maximum absorbance of chlorophyll and at 720 nm there is the point of minimum absorbance of chlorophyll.

The previously defined absorbance index AD is able to determine the quality and ripeness of fruit, said index AD is set by the difference between the absorbance at the two aforesaid wavelengths (FIG. 5):

$$AD \text{ (absorbance difference)} = A(670 \text{ nm}) - A(720 \text{ nm}).$$

Figure 6:
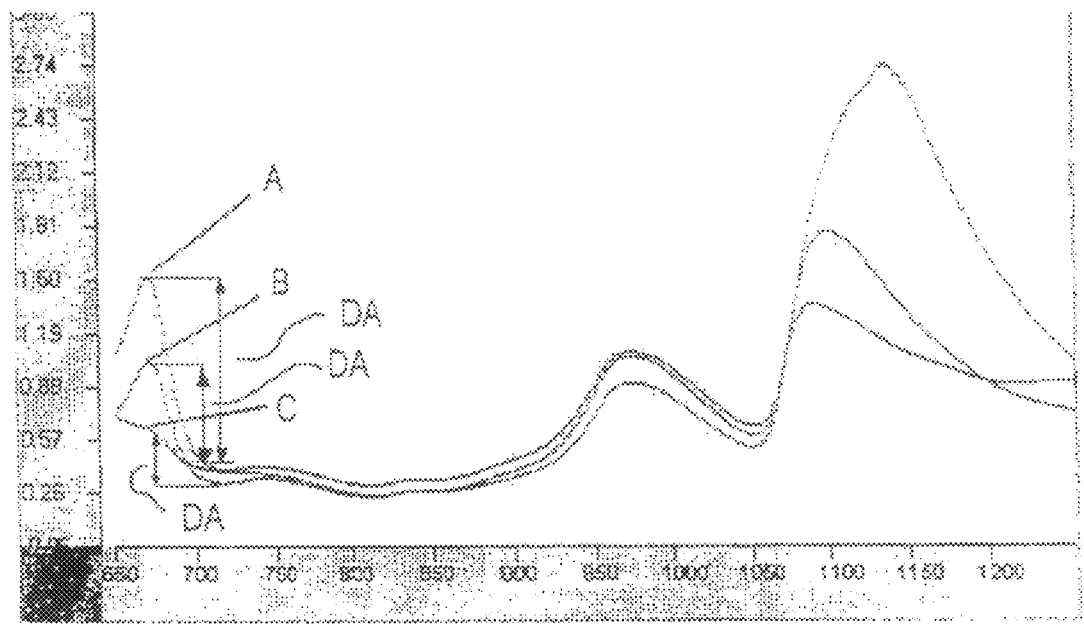
FIGS. 6 and 7 illustrate two diagrams of the absorbance of the chlorophyll in function of the wavelength of electromagnetic radiation for two types of fruit at different degrees of ripeness.
Figure 7:
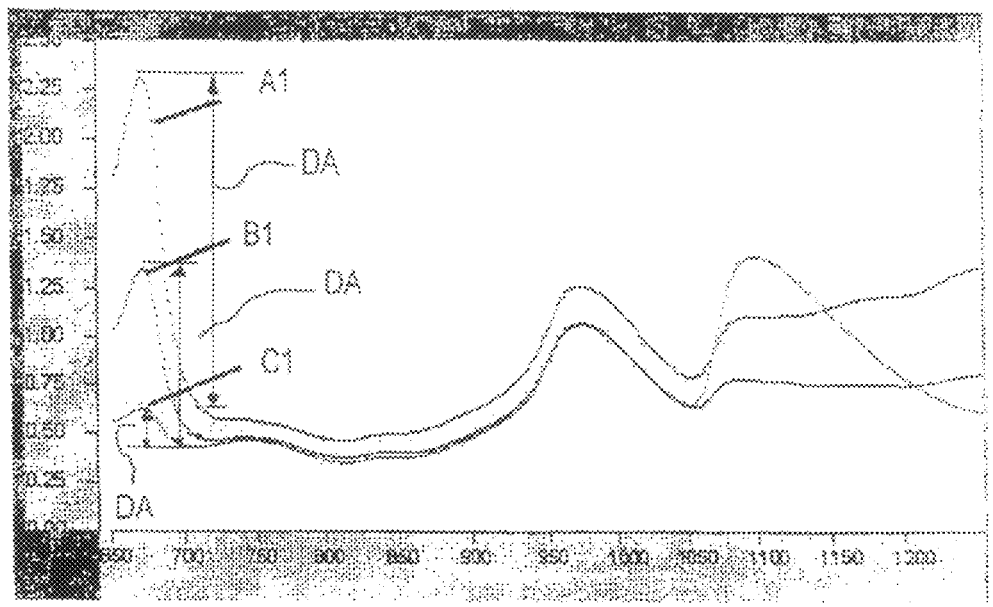

FIGS. 6 and 7 indicate, respectively for peaches and apples, three chlorophyll absorption spectra at three different ripening stages—curves A, B, C and curves A1, B1, C1—the curves A, A1 refer to unripe peaches and apples, the curves B, B1 refer on the other hand to peaches and apples in which ripening has already started, lastly, the curves C, C1 refer to ripe peaches and applies.

Analysing FIGS. 6 and 7 it can be noted that the index AD, which was previously defined and illustrated in FIG. 5, varies in function of the ripening of the fruit, progressively decreasing the value thereof.

With the measurement of the index AD, which is obtained with the apparatus 1 and the method according to the invention, satisfactory results are also obtained on fruit that ripens without significantly varying the colour of the skin because part of the skin and part of the pulp is considered.

The measurement of the index AD, obtained with the apparatus 1 and the method according to the invention, is independent of the temperature. It has in fact been found that whilst the absorbance values at the two wavelengths 670 nm and 720 nm vary with the temperature, the difference between these two absorbance values does not change with the temperature, and this prevents having to perform laborious and uncertain compensations or calibrations to take account of temperature variations.

As a result, the index AD can be measured also on products that have different temperature conditions, i.e. a fruit can be measured when it has just left the refrigerator or when it has just been picked from the plant on a day in the middle of summer, without the need to repeat calibrations according to the temperature reached by the fruit.

Figure 8:
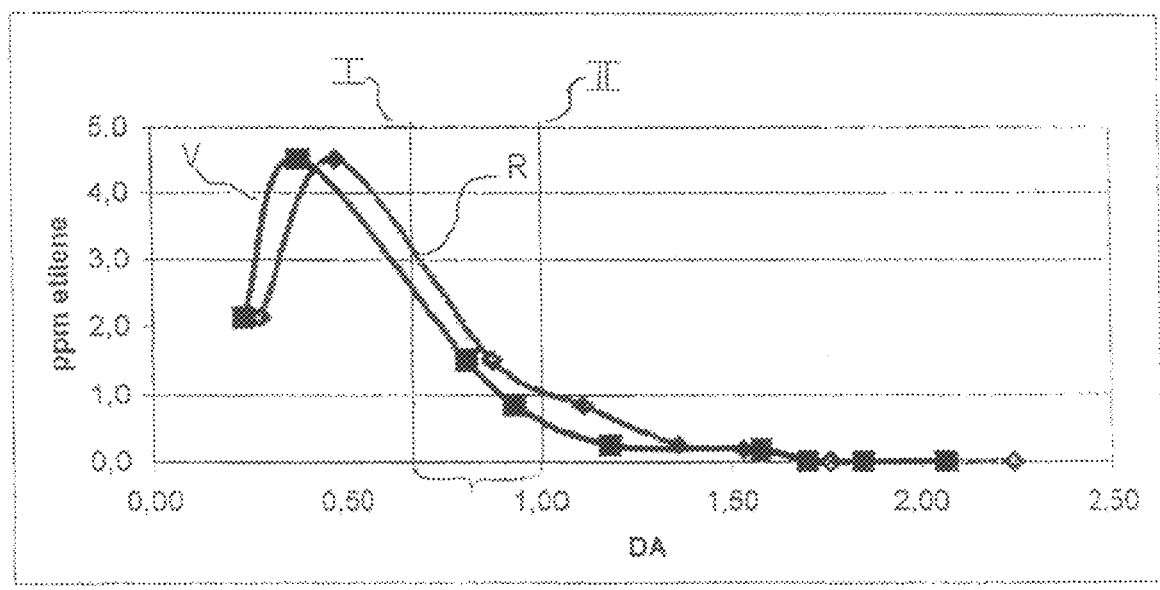
FIG. 8 illustrates a diagram of the pattern of ethylene concentration on two different sides of a fruit in function of an AD index.

In FIG. 8 there is illustrated the relationship that exists between the index AD, measured both from the green side (line V) and from the red side (line R) of the fruit, in function of the ethylene (ppm: parts per million) issued by a fruit, during the cultivar Gala harvest.

The two vertical lines "I" and "II" indicate the optimal AD range within which harvesting should occur.

It is also important to emphasise that the index AD does not vary between the two sides of the fruit. This indicates that the differences in colouring due to a differential accumulation of other pigments such as carotenoids and anthocyanins do not affect the recorded spectra. This aspect is of fundamental importance as it frees the spectrometric measurement from the portion of the fruit in which it was conducted.

Another important aspect of the invention, is that the measurement is made on a layer of fruit and it is therefore independent of the size of the fruit.

Figure 9:
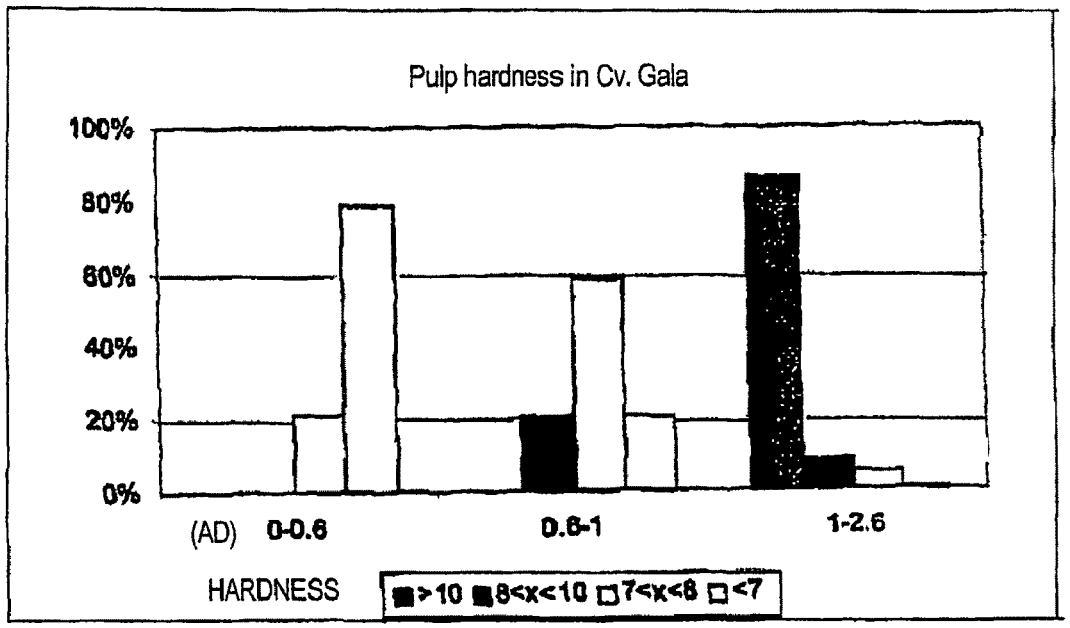
FIGS. 9 and 10 illustrate two statistical diagrams of the AD index in function of some typical features of fruit.
Figure 10:
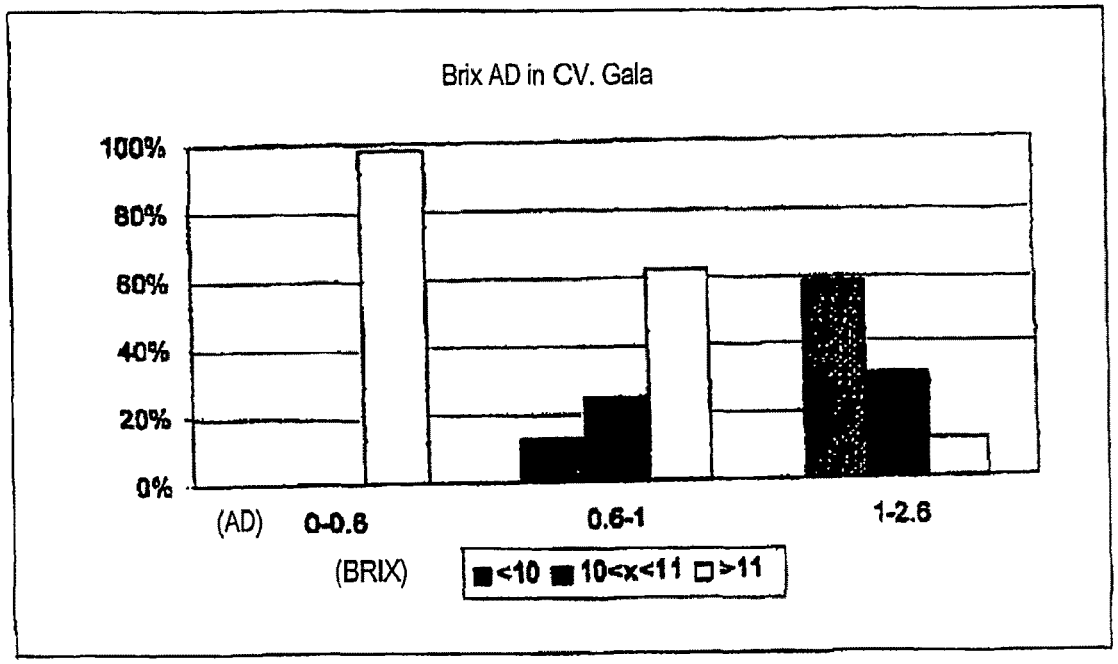

In FIG. 9 there is illustrated the relationship that exists between the index AD and the hardness classes (in kg/cm$^2$), whilst in FIG. 10 there is illustrated the relationship that exists between the index AD and the content in soluble solids (expressed in Brix grades), still of the cultivar Gala.

The publications regarding the definition of the best harvesting index for fruit have led 1 ppm of ethylene to be defined as the minimum level that a fruit has to have to reach an optimal organoleptic quality at the end of conservation.

Owing to the aforesaid ethylene value, the range of the index AD is defined between 0.6 and 1 as the best range for obtaining an excellent product at the end of conservation.

In support of what has been said before, the graphs of FIGS. 9 and 10 can be observed in which it is noted that 80% of the fruit that is included in the range AD=0.6-1 reaches hardness values of the lower pulp that are lower than 8 kg/cm$^2$ (FIG. 9), and that 83% of the fruit reaches a refractometric grade that is greater than 10° Brix (FIG. 10).

As far as the other two intervals are concerned, interval AD=1-2.6 relates to products in the ripening phase, and which are therefore not yet ready for harvesting, whilst the fruits in the range AD=0-0.6 have all the requirements necessary for being defined optimal and must therefore be directed directly to consumption or conservation for a short period.

It is obvious that the apparatus according to the invention, by means of the measurement of the index AD, enables all the information to be obtained that is necessary for evaluating the quality of the fruit. The same product management can be improved and facilitated, enabling the use of instruments, completely objective assessments and which are no longer dependent on the judgement of operators who are sometimes not completely competent.

Examples of species that can be investigated with the apparatus according to the invention are: peach, apple, actinidia, pear, plum, apricot, strawberry, cherry, melon, water-melon. Another important advantage of the invention is that it is not necessary to conduct a long series of destructive tests to obtain reliable results on the quality of the fruits.

With the techniques that are currently available for assessing the quality of the fruit it is necessary to conduct a great number of experiments, i.e. to measure the graphs of the spectrometer and the graphs comparing with the values of the parameters of the fruits measured in a conventional and known manner; the results of these comparisons are processed with appropriate statistical techniques, such as for example linear multiple regression, programming fractional factorial experiments and other statistical methods.

With the apparatus according to the invention this is no longer necessary because the index AD is based on the difference of two absorbance values and so smaller variability factors are present.

In order to prepare the apparatus according to the invention to evaluate the quality of a new variety (of fruit) only a few initial tests are necessary to identify the relationship between the AD value ranges and the qualitative parameters of the products.

Figure 11:
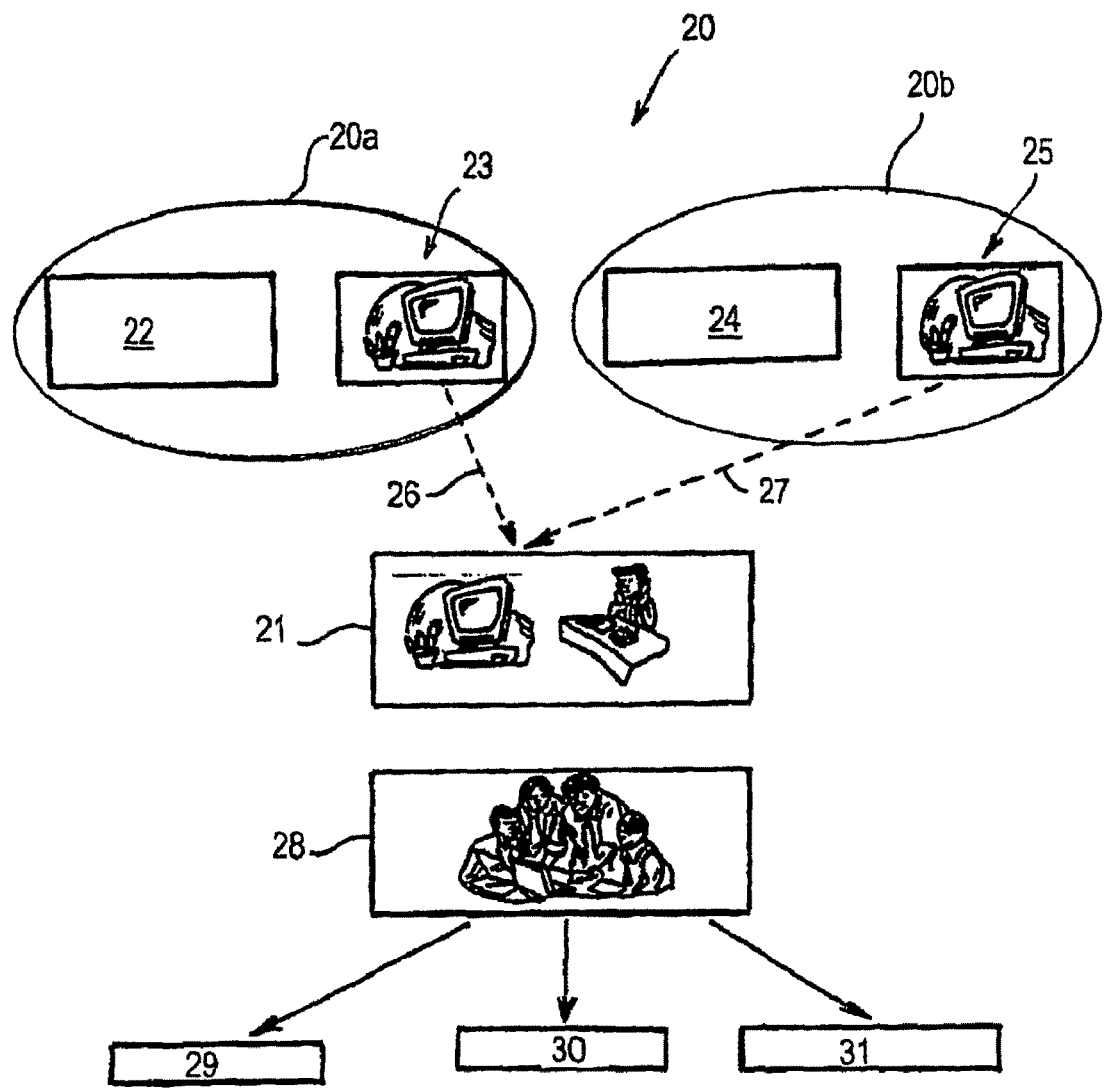
FIG. 11 illustrates a diagram of a data acquisition system relating to various cultivation and harvesting centres that use an apparatus according to the invention.
Figure 12:
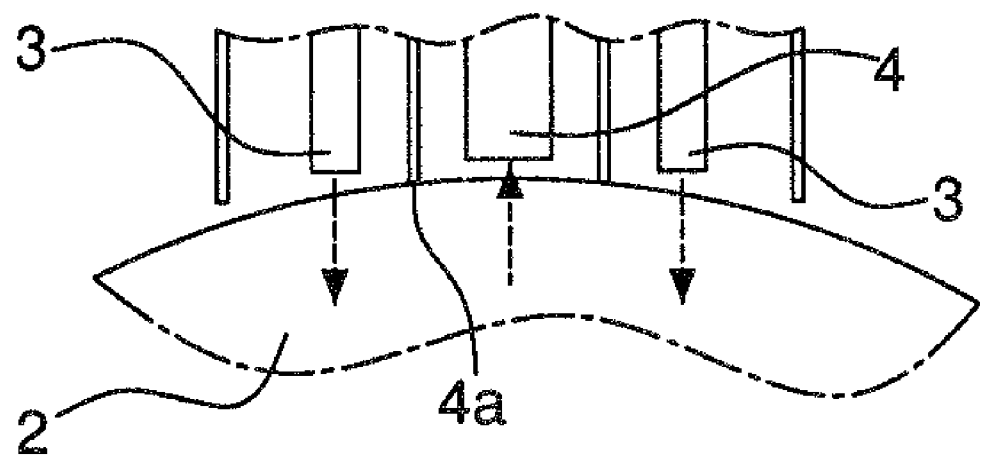
FIG. 12 is a schematic cross-section of a sensor and light source arranged adjacent a generic piece of fruit.

In FIG. 11 there is illustrated a control and archiving system 20 of network or wireless type, comprising a central archive 21 that has the object of receiving all the data coming from the company cultivation and harvesting centres 20a, 20b, etc.

The measurements for each company centre 20a, 20b, are obtained with apparatuses 22, 24 according to the invention. Said apparatuses 22, 24 transfer the data of the measurements performed at the company centres to personal computers or palmtop computers 23, 25. The personal computers or palmtop computers 23, 25, in turn send the data on the measurements by means of a network 26, 27, which can also be of wireless type, to the central archive 21 that is also realised with a computer.

All the data on the products 2 originating from each company centre 20a, 20b are examined and compared with the optimal values by means of the a comparison device 28.

On the basis of the result of the comparison, the products can be sent to a storage facility 29 or to a supermarket 30 or to small retail outlets 31.

The system 20 that is thus studied enables the physical and chemical features of the products to be obtained in real time, the production thereof to be estimated, etc.

Furthermore, the harvesting date of the products can also be estimated with a certain precision, it is in fact possible to check the ripening of the fruit that is still attached to the tree.

The invention claimed is:

1. A method for determining the quality and ripeness of fruit and vegetable products, the method comprising the steps of:
    irradiating a fruit or vegetable product with radiating light;
    measuring the absorbance of the product at two wavelengths corresponding to maximum and minimum absorption values of chlorophyll by a sensor isolated from the light reflected by the surface of the product;
    determining the difference of absorbances measured at said two wavelengths, said difference being correlated with at least one parameter used to measure product ripeness.

2. The method according to claim 1, comprising correlating said difference to various parameters used to measure product quality and ripeness including: ethylene concentration, pulp firmness and Brix grades.

3. The method according to claim 1, wherein said radiating light has a wavelength centred on at least a value of 670 nm plus or minus a range of 50 nm.

4. The method according to claim 1, wherein the radiating light is radiated through a sealed aperture in contact with the surface of the product.

5. The method according to claim 1, wherein a return radiation from the product at said wavelengths is measured through a sealed aperture in contact with the product surface.

6. The method according to claim 5, wherein the return radiation at said wavelengths is measured through an aperture separated from a surface irradiated with radiating light.

7. The method according to claim 1, wherein a product is irradiated with radiating light at wavelengths of 670 nm and 720 nm.

8. The method according to claim 1, wherein said two wavelengths are 670 nm and 720 nm.

9. An apparatus for determining the quality and ripeness of fruit and vegetable products, the apparatus comprising:
- a radiating light source;
- a detecting device for detecting a return radiation from the fruit and vegetable products at wavelengths of 670 nm and 720 nm;
- a sensor to receive part of the return radiation from the fruit and vegetable products, said sensor being connected to said detecting device, said sensor having a separating element to prevent radiation originating from said source from reaching said sensor directly without passing through the product;
- a differentiating and amplifying device designed to provide an absorbance difference signal measuring the difference of absorbance at said wavelengths of 670 nm and 720 nm;
- a central control and processing unit for processing said absorbance difference signal received from said differentiating and amplifying device; and
- a display for displaying the result of said processed signal.

10. The apparatus according to claim 9, wherein the radiating light source emits radiation at a wavelength of 670 nm and a bandwidth of plus or minus 50 nm.

11. The apparatus according to claim 9, wherein the detecting device comprises a detector.

12. The apparatus according to claim 11, wherein said detector comprises a photodiode.

13. The apparatus according to claim 11, wherein said detector comprises a spectrometer.

14. The apparatus according to claim 11, wherein the detecting device comprises an optic filter.

15. The apparatus according to claim 14, wherein the optic filter is inserted between the source and the detector.

16. The apparatus according to claim 14, wherein the optic filter filters radiation at the wavelengths of 670 nm and 720 nm.

17. The apparatus according to claim 9, wherein the radiating light source comprises LEDs, a laser beam, a white light source or a white filtered light source.

18. The apparatus according to claim 17, wherein the radiating light source is electrically powered by a power supply stabilizing device which maintains radiating light emitted by the radiating light source at a constant level.

19. The apparatus according to claim 9, wherein the central control and processing unit processes the absorbance difference signal and correlates this with product quality features such as ethylene concentration, pulp firmness and Brix grades.

20. The apparatus according to claim 19, wherein the central control and processing unit processes the absorbance difference signal and, on the basis of the degree of ripeness, classifies the product as ripe, not ripe, to be stored and generates a signal relating to product quality.

21. The apparatus according to claim 20, wherein the central control and processing unit sends the signal relating to product quality to the display.

22. The apparatus according to claim 9, wherein the display comprises a series of LEDs.

23. The apparatus according to claim 9, wherein the display comprises a screen.

24. The apparatus according to claim 22, wherein each LED indicates a different stage in the quality of the product considered.

25. The apparatus according to claim 22, comprising an adjusting unit for adjusting the threshold at which the LEDs light up.

26. The apparatus according to claim 9, comprising a memory device designed to store data received from the central control and processing unit.

27. The apparatus according to claim 9, comprising an interface for being connected to a computer in order to enable a transfer of data from the central control and processing unit.

28. The apparatus according to claim 9, comprising a battery-powered electricity supply.

29. The apparatus according to claim 9, wherein the apparatus is contained inside a casing containing all the components of apparatus.

30. The apparatus according to claim 9, wherein the apparatus is of the portable type.

* * * * *